United States Patent [19]

Sun et al.

[11] Patent Number: 4,970,226
[45] Date of Patent: Nov. 13, 1990

[54] BIS-INDOLE IMIDAZOLE COMPOUNDS WHICH ARE USEFUL ANTITUMOR AND ANTIMICROBIAL AGENTS

[75] Inventors: H. Howard Sun, Glenmoore, Pa.; Shinichi Sakemi, Aichi, Japan; Sarath Gunasekera, Vero Beach, Fla.; Yoel Kashman, Tel Aviv, Israel; May Lui, Sabastian, Fla.; Neal Burres, Highland Park, Ill.; Peter McCarthy, Vero Beach, Fla.

[73] Assignee: Harbor Branch Oceanographic Institution, Inc., Fort Pierce, Fla.

[21] Appl. No.: 416,338

[22] Filed: Oct. 3, 1989

[51] Int. Cl.$^5$ ............................................. A61K 31/415
[52] U.S. Cl. ...................................... 514/397; 548/336
[58] Field of Search ........................ 548/336; 514/397

[56] References Cited

U.S. PATENT DOCUMENTS

| | | | |
|---|---|---|---|
| 4,548,814 | 10/1985 | Rinehart, Jr. | 424/95 |
| 4,729,996 | 3/1988 | Wright et al. | 514/215 |
| 4,737,510 | 4/1988 | Rinehart, Jr. | 514/388 |
| 4,808,590 | 2/1989 | Higa et al. | 514/272 |

OTHER PUBLICATIONS

Faulkner, D. J. (1984) Natural Products Reports 1:551–598.
Faulkner, D. J. (1986) Natural Products Reports 3:1–33.
Faulkner, D. J. (1987) Natural Products Reports 4(5):539–576.
Faulkner, D. J. (1988) Natural Products Reports 5:613–663.
Uemura, D. et al., (1985) "Norhalichondrin A: An Antitumor Polyether Macrolide from a Marine Sponge," J. Am. Chem. Soc. 107:4796–4798.
Moquin, C. and M. Guyot (1984) "Grossularine, A Novel Indole Derivative from the Marine Tunicate, *Dendrodoa grossularia*," Tetrahedron Letters 25(44):5047–5048.
Norton, R. S., and R. J. Wells (1982) "A Series of Chiral Polybrominated Bindoles from the Marine Blue-Green Alga Rivularia firma, Application of $^{13}$C NMR Spin-–Lattice Relaxation Data and $^{13}$C-$^1$H Coupling Constants to Structure Elucidation," J. Am. Chem. Soc. 104:3628–3635.
Bartik, K. et al., (1987) "Topsentins, New Toxic Bis-Indole Alkaloids from the Marine Sponge *Topsentia genitrix*," Can. J. Chem. 65:2118–2121.
Braekman, J. C. et al., (1987) "Synthesis of Topsentin-A, a Bisindole Alkaloid of the Marine Sponge Topsentia genitrix," Bull. Soc. Chim. Belg. 96(10):809–812.

*Primary Examiner*—Mary C. Lee
*Assistant Examiner*—Zinna Northington Davis
*Attorney, Agent, or Firm*—Saliwanchik & Saliwanchik

[57] ABSTRACT

Novel brominated bisindole-imidazole alkaloids have been isolated from marine sponges. These compounds, and derivatives thereof, are useful antimicrobial and antitumor compounds.

24 Claims, 1 Drawing Sheet

|              | X1 | X2 |
|--------------|----|----|
| Nortopsentin A | Br | Br |
| Nortopsentin B | H  | Br |
| Nortopsentin C | Br | H  |
| Nortopsentin D | H  | H. |

BIS-INDOLE IMIDAZOLE COMPOUNDS WHICH ARE USEFUL ANTITUMOR AND ANTIMICROBIAL AGENTS

BACKGROUND OF THE INVENTION

Considerable research and resources have been devoted to oncology and antitumor measures including chemotherapy. While certain methods and chemical compositions have been developed which aid in inhibiting, remitting, or controlling the growth of tumors, new methods and antitumor chemical compositions are needed. The prevention and control of fungal growth is also of considerable importance to man, and much research has been devoted to the development of antifungal measures.

It has been found that some natural products and organisms are potential sources for chemical molecules having useful biological activity of great diversity. Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,808,590 discloses compounds, having antiviral, antitumor, and antifungal properties, isolated from the marine sponge Theonella sp.; and U.S. Pat. No. 4,737,510 discloses compounds, having antiviral and antibacterial properties, isolated from the Caribbean sponge *Agelas coniferin*. Clearly, marine sponges have proved to be a source of biological compounds, and a number of publications have issued disclosing organic compounds derived from marine sponges, including Scheuer, P. J. (ed.) *Marine Natural Products, Chemical and Biological Perspectives*, Academic Press, New York, 1978-1983, Vol. I-V; Faulkner, D. J., (1984) Natural Products Reports 1:551-598; Natural Products Reports (1986) 3:1-33; Natural Products Reports (1987) 4:539-576; Natural Products Report (1988) 5:613-663; J. Am. Chem. Soc. (1985) 107:4796-4798.

The subject invention concerns novel bisindole-imidazole alkaloids. Indole compounds of marine origin have previously been described in Tetrahedron Letters (1984) 25:5047-5048 and J. Am. Chem. Soc. (1982) 104:3628-3635. See also Bartik, K., J. C. Braekman, D. Daloze, C. Stoller, J. Huysecom, G. Vandevyer, and R. Ottinger (1987) Can. J. Chem. 65:2118; and Braekman, J. C., D. Daloze, and C. Stoller (1987) Bull. Soc. Chi. Belg. 96(10):809.

The present invention, utilizing sponges as a source material and supplemented by novel synthetic production methods, has provided the art with a new class of biologically active compounds and new pharmaceutical compositions useful as antitumor and antimicrobial agents.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The subject invention concerns novel brominated bisindole-imidazole alkaloids and methods for use of these compounds. Specifically exemplified herein are six novel compounds. Three of these compounds—nortopsentin A, nortopsentin B, and nortopsentin C—were isolated from marine sponges Topsentia and Halichondria spp. These compounds, as well as their derivatives, show antitumor and antimicrobial activities. Thus, this new class of compounds and their derivatives and analogs could be used as antitumor and/or antimicrobial agents.

The isolation of the natural products was performed using solvent partition and centrifugal countercurrent chromatography. The final purification of nortopsentin A, B, and C was achieved using HPLC, prep TLC and recrystallization, respectively. The structures of nortopsentins were determined mainly on the basis of their $^1$H and $^{13}$C NMR data. The deduced structures of the novel compounds are shown in FIG. 1.

The compounds of the subject invention, including derivatives and salts thereof, have antitumor and antimicrobial properties. Thus, they can be used for the treatment of a number of diseases, including cancer.

DETAILED DESCRIPTION OF THE INVENTION

Figure 1:
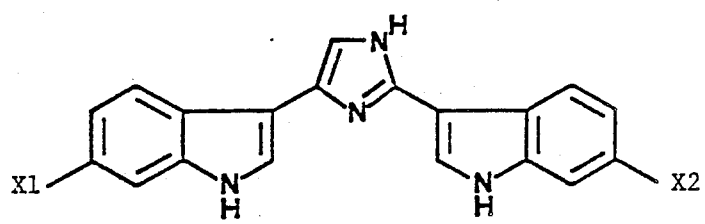
FIG. 1 shows the deduced structures of the novel compounds.

The subject invention pertains to novel chemical compounds isolated from marine sponges. These compounds have been shown to possess antitumor and antimicrobial activity. Thus, the subject invention pertains to the compounds themselves, as well as pharmaceutical compositions containing these compounds. Also disclosed and claimed are methods for administering the novel compositions. Various derivatives of these compounds can be produced by known procedures. Simple salts of the compounds described here are also within the scope of the invention. These simple salts could include, for example, the $Cl^-$, $Br^-$, $I^-$, and $HSO_4^-$ salts. As is known by those skilled in the art, these salts can be produced using, for example, anion exchange columns. The parent compounds can be isolated from marine sponges as described below.

Following are examples which illustrate procedures, including the best mode, for practicing the invention. These examples should not be construed as limiting. All percentages are by weight and all solvent mixture proportions are by volume unless otherwise noted.

EXAMPLE 1—ISOLATION OF NORTOPSENTIN A, B, & C

The sponge Spongosorites sp. (80 g), collected at the depth of 630 ft. off Chub Cay, Bahamas, on Aug. 26, 1985, was lyophilized and extracted with methanol-toluene (3:1). The extract was evaporated to dryness and partitioned between ethyl acetate and water. The water soluble fraction was further partitioned with butanol. The combined ethyl acetate and butanol fractions were chromatographed on a Hibar LiChrosorb $NH_2$ column using HPLC with $CHCl_3$—MeOH (5:1) as elution solvent to yield a semi-purified compound, nortopsentin B (3 mg).

Sponge of the genus Halichondria (830 g) was collected at the depth of 1512 ft. off Nassau, Bahamas, on Mar. 15, 1987. The frozen sponge was extracted with 1.5L of methanol four times. The extracts were combined and concentrated under reduced pressure to give a 400 mL of water suspension, which was then extracted with ethyl acetate (300 mL×3). The resulting ethyl acetate fraction was evaporated to dryness to yield a crude fraction (12.02 g). It was found that the majority of the components in this fraction was topsentin and bromotopsentin.

A two-phase solvent system was generated by mixing heptane, ethyl acetate, methanol, and water in a ratio of 4:7:4:3. The crude fraction (12.00 g) was partitioned between 150 ml of the upper phase solvent and 300 ml of the lower phase solvent. The resulting lower layer fraction was extracted with 150 ml of the upper phase solvent three more times. The combined upper layer fractions were evaporated to dryness (5.75 g) and dissolved in 50 ml of the upper phase solvent. The solids were filtered off and the eluant was evaporated to dryness (4.46 g). The residue was dissolved again in 30 ml of the upper phase solvent. After removal of the insoluble material and evaporation of the solvent, 2.75 g of a solid was obtained.

This solid was further fractionated by using centrifugal countercurrent chromatography with two different solvent systems consisting of heptane/ethyl acetate/methanol/water in ratios of 4:7:4:3 and 5:7:4:3. A fraction containing nortopsentin A and a mixture of nortopsentin B and C along with topsentin (400 mg) and bromotopsentin (540 mg) were obtained. Nortopsentin A (250 mg) was purified by HPLC on a Hibar $NH_2$ column (10×250 mm), using 5:1 chloroform/methanol as eluant. Preparative TLC (Kieselgel $60F_{264}$, 2 mm thickness, ethyl acetate) afforded a pure nortopsentin C (200 mg) and a fraction containing nortopsentin B. Pure nortopsentin B (250 mg) was finally recrystallized from ethyl acetate/chloroform.

EXAMPLE 2—PHYSICAL AND SPECTRAL DATA OF NORTOPSENTIN A

Nortopsentin A, a colorless oil; HREIMS m/z 453.9426 (calcd. for $C_{19}H_{12}N_4Br_2$, $\Delta 0.3$ mmu); LREIMS m/z 457.9(31.8), 455.9(57.7), 453.9(29.4), 377.0(9.5), 375.1(9.4), 350.0(1.8), 348.0(2.2), 296.1(4.7), 268.1(3.2), 236.0(4.9), 234,0(5.7), 222.0(5.0), 219.9(5.1), 209.0(6.8), 207.0(7.2), 197.0(7.0), 195.0(7.3), 188.6(7.4), 155.1(16.2), 148.1(7.3), 141.0(7.2), 128.0(25.6), 116.1(10.9), 114.1(9.6), 101.0(12.8), 89.0(6.9), 82.0(23.3), 79.9(24.4), 77.0(7.2), 75.1(7.7), 63.1(6.6), 58.1(6.2), 51.0(6.0), 44.1(62.5), 32.0(52.6), and 28.2(100.0 rel. %); LRFABMS m/z 459, 457, and 455 for $(M+H)^+$; UV(MeOH) $\lambda$max 207.0($\epsilon$50,300), 236.0($\epsilon$42,300), 277.0($\epsilon$26,400), and 310(sh) nm; IR(KBr) 3420, 1615(sh), 1591, 1510, 1448, 1430(sh), 1328, 1248, 1100, 1023, 919, 892, 800, 781, and 757 $cm^{-1}$; $^1$H NMR(acetone-$d_6$) $\delta$11.059(1H, brs, $D_2O$ exchangeable), 10.847(1H, brs, $D_2O$ exchangeable), 8.469(1H, d, J=8.5 Hz), 7.996(1H, d, J=8.5 Hz), 7.901(1H, d, J=2.1 Hz), 7.795(1H, d, J=2.3 Hz), 7.618(1H, d, J=1.8 Hz), 7.610(1H, d, J=1.8 Hz), 7.530(1H, s), 7.319(1H, dd, J=8.4 Hz), and 7.298(1H, dd, J=8.4, 1.6 Hz); $^{13}$C NMR(acetone-$d_6$) $\delta$143.77(s), 138.46(s), 138.26(s), 133.34(s, br), 125.09(s×2), 125.02(d, J=185 Hz), 123.79(d, J=166 Hz), 123.49(d, J=184 Hz), 123.31(d, J=164 Hz), 123.18(d, J=165 Hz), 122.26(d, J=161 Hz), 116.16(s), 166.10(d, br, J=189 Hz), 115.52(s), 115.24(d, J=166 Hz), 115.18(d, J=166 Hz), 110.71(s), and 108.72(s); $^1$H NMR(methanol-$d_4$) $\delta$8.401(1H, d, J=8.5 Hz), 7.718(1H, d, J=8.5 Hz), 7.695(1H, s), 7.609(1H, s), 7.545(1H, d, J=1.7 Hz), 7.536(1H, d, J=1.7 Hz), 7.297(1H, s), 7.245(1H, dd, J=8.5, 1.7 Hz), and 7.196(1H, dd, J=8.5, 1.7 Hz); $^{13}$C NMR(methanol-$d_4$) $\delta$144.31(s), 138,88(s), 138.70(s), 132.67(s, br), 125.59(d, J=183. Hz), 125.38(s), 125.16(s), 124.24(d, J=165 Hz), 123.60(d×2, J=183 and 164 Hz), 122.62(d, J=162 Hz), 121.95(d, J=161 Hz), 117.57(d, br, J=191 Hz), 116,67(s), 116.18(s), 115.39(d, J=166 Hz), 115.30(d, J=166 Hz), 110.04(s), and 108.43(s).

EXAMPLE 3—PHYSICAL AND SPECTRAL DATA OR NORTOPSENTIN B

Nortopsentin B, colorless crystals; decomposed at 250°-270° C.; HREIMS m/z 376.0320(calcd. for $C_{19}H_{13}N_4Br$, $\Delta 0.4$ mmu), LREIMS m/z 378.1(55.5), 376.2(56.7), 350.1(2.8), 348.1(2.5), 297.1(19.7), 270.1(5.1), 268.1(5.1), 242,1(3.8), 236.0(6.9), 234.0(6.6), 209.0(4.4), 207.1(4.3), 188.0(6.8), 155.1(37.1), 148.5(26.8), 142.1(10.7), 135.1(11.9), 128.0(47.3), 121.1(9.1), 114.1(12.1), 101.0(28.4), 82.0(46.3), 79,9(50.8), 77.1(16.3), 75.1(17.6), 63.2(9.7), 58.2(19.1), 51.0(15.6), 44.1(100.0), 39.8(23.6), 32.0(100.0), and 28.2(100.0 rel. %); LRFABMS m/z 379 and 377 for $(M+H)^+$; UV(MeOH) $\lambda$max 206.5($\epsilon$50,700), 232.0($\epsilon$45,200), 278.5($\epsilon$25,600), and 310(sh) nm; IR(KBr) 3400, 1620(sh), 1603(sh), 1587, 1562(sh), 1448, 1422, 1364, 1328, 1249, 1238, 1104(br), 1092(sh), 1024, 927(sh), 920, 894, 811, 762, and 743 $cm^{-1}$; $^1$H NMR(acetone-$d_6$) $\delta$10.709(1H, brs), 10.378(1H, brs), 8.540(1H, d, J=8.5 Hz), 8.029(1H, brd, J=7.4 Hz), 7.916(1H, d, J=2.7 Hz), 7.743(1H, d, J=2.3 Hz), 7.648(1H, d, J=1.7 Hz), 7.443(1H, dd, J=8.7, 1.3 Hz), 7.426(1H, s), 7.290(1H, dd, J=8.6, 1.8 Hz), 7.152(1H, m), and 7.114(1H, m); $^{13}$C NMR(acetone-$d_6$) $\delta$143.38(s), 138.44(s), 137.86(s), 126.34(s), 125.47(s), 124.27(d×2), 123.67(d), 122.45(d), 122.35(d), 120.97(d), 120,15(d), 116.04(s), 115.09(d), 112.30(d), and 109.61(s); $^1$H NMR(1:1 acetone-$d_6$/methanol-$d_4$) $\delta$8.259(1H, d, J=8.5 Hz), 7.942(1H, brd, J=8.6 Hz), 7.864(1H, s), 7.758(1H, s), 7.616(1H, d, J=1.7 Hz), 7.463(1H, s), 7.429(1H, brd, J=8.5 Hz), 7.284(1H, dd, J=8.5, 1.7 Hz), 7.165(1H, m) and 7.131(1H, m); $^{13}$C NMR(1:1 acetone-$d_6$/methanol-$d_4$) $\delta$143.85(s), 138.58(s), 137.97(s), 132,89(s, br), 126.37(s), 125.50(d), 125.26(s), 124.09(d), 123.24(d), 122.89(d), 122.75(d), 120.75(d), 120.60(d), 118.01(d, br), 116.40(s), 115.45(d), 112.60(d), 109.77(s, br), and 108.86(s).

EXAMPLE 4—PHYSICAL AND SPECTRAL DATA OF NORTOPSENTIN C

Nortopsentin C, a colorless oil; HREIMS m/z 376.0316 (calcd. for $C_{19}H_{13}N_4Br$, $\Delta 0.8$ mmu); LREIMS m/z 378.1(95.7), 376.1(100.0), 350.0(5.3), 348.1(5.3), 297.1(20.3), 270.1(6.6), 268.1(6.4), 242.1(5.8), 235.0(5.6), 233.0(4.9), 209.0(8.8), 207.0(8.9), 197.0(7.0), 195.0(7.4), 188.0(9.7), 155.1(45.0), 148.5(38.1), 142.1(14.6), 135.1(14.5), 128.0(51.4), 116.1(19.4), 101.0(35.5), 89.0(15.0), 81.9(30.5), 79.8(30.7), 58.1(28.5), and 53.1(24.5 rel. %); LRFABMS m/z 379 and 377 for $(M+H)^+$; UV(MeOH) $\lambda$max 207.5($\epsilon$50,300), 230(sh), 280(sh) and 310(sh)nm; IR(KBr) 3410, 1620(sh), 1598, 1450, 1531(br), 1411(br), 1332, 1245, 1128, 1100, 1023, 920, 896, 800, and 745 $cm^{-1}$; $^1$H NMR(acetone-$d_6$) $\delta$10.598(2H, brs), 8.552(1H, brd, J=8.7 Hz), 8.038(1H, d, J=8.5 Hz), 7.892(1H, d, J=2.1 Hz), 7.756(1H, br, J=2.1 Hz), 7.615(1H, d, J=1.0 Hz), 7.447(1H, dd, J=8.8, 2.5 Hz), 7.434(1H, s), 7.243(1H, dd, J=8.7, 1.7 Hz), 7.181(1H, m), and 7.160(1H, m); $^{13}$C NMR(acetone-d$_6$) δ144.41(s), 138.65(s), 137.67(s), 126.38(s), 125.44(s), 123.82(d), 123.34(d), 123.09(d), 122.91(d), 122.72(d), 122.32(d), 120.70(d), 115.40(s), 115.15(d), 112.30(d), and 109.13(s); $^1$H NMR(methanol-d$_4$) δ8.208(1H, m), 7.754(1H, s), 7.747(1H, d, J=8.4 Hz), 7.637(1H, s), 7.549(1H, d, J=1.6 Hz), 7.405(1H, m), 7.330(1H, s), 7.218(1H, dd, J=8.6, 1.7 Hz), 7.194(1H, m), and 7.169(1H, m); $^{13}$C NMR(methanol-d$_4$) δ145.01(s), 138.86(s), 137.91(s), 132.65(s, br), 126.20(s), 125.38(s), 124.98(d), 123.58(d×2), 123.25(d), 121.16(d), 121.06(d), 117.25(d, br), 116.15(s), 115.27(d), 112.54(d), 110.18(s), and 108.10(s).

EXAMPLE 5—NORTOPSENTIN D

The derivative designated nortopsentin D has the structure shown in FIG. 1 wherein X1 is H and X2 is H. This compound can be readily prepared from nortopsentin A, B, or C by catalytic hydrogenation at room temperature and atmospheric pressure.

EXAMPLE 6—PREPARATION OF TRIMETHYL—AND TETRAMETHYLNORTOPSENTIN B

Nortopsentin B (23.0 mg) was treated with dimethyl sulfate (1.0 ml) and K$_2$CO$_3$ (30 mg) in dry acetone at room temperature for 16 hours. The reaction mixture was filtered and separated on silica TLC plates (Kieselgel 60F$_{254}$, 1 mm thickness, 5:1 chloroform/methanol) to afford 8.5 mg of trimethylnortopsentin B and 19.7 mg of tetramethylnortopsentin B as methyl sulfate salts. Their chloride salts were prepared by passing through a strong anion exchange column (Baker, Solid Phase Extraction Column, Quaternary amine, Cl$^-$ form) with 1:1 methanol/water.

Trimethylnortopsentin B (MeSO$_4^-$ salt), colorless crystals, crystallized from chloroform/ethyl acetate; mp. 116°-118° C.; HREIMS m/z 404.0631(calcd. for C$_{21}$H$_{17}$N$_4$Br=M$^+$+H—CH$_3$, Δ0.6 mmu); LREIMS m/z 419.9(0.5), 417.9(0.5), 405.9(3.7), 403.9(3.8), 280.9(2.6), 207.0(25.0), 190.9(3.6), 169.0(2.6), 155.0(1.9), 141.9(5.0), 133.0(4.0), 96.0(27.3), 94.0(28.6), 82.0(14.1), 79.8(15.1), 64.0(49.2), and 44.1(100.0 rel %); UV(Cl$^-$ salt, MeOH) λmax 200.0(ε37,800), 217.5(ε48,200), 272(sh), 280(ε20,700), 287.5(ε21,100), 293.5(ε19,300), and 314(sh) nm; IR(Cl$^-$ salt, KBr) 3400, 1625, 1615(sh), 1580, 1561, 1525, 1495(br), 1450, 1420(sh), 1363, 1340, 1322, 1296, 1245, 1228, 1185, 1157, 1137, 1105, 1053, 1013, 978, 944, 811, and 750 cm$^{-1}$; $^1$H NMR(MeSO$_4^-$ salt, acetone, d$_b$) δ11.416(1H, br), 8.276(1H, s), 7.944(1H, s), 7.919(1H, d, J=1.7 Hz), 7.879(1H, d, J=2.8 Hz), 7.734(1H, brd, J=7.8 Hz), 7.666(1H, d, J=8.5 Hz), 7.630(1H, brd, J=8.0 Hz), 7.411(1H, dd, J=8.4, 1.7 Hz), 7.233(1H, ddd, J=8.3, 7.0, 1.3 Hz), 7.161(1H, ddd, J=8.3, 7.0, 1.3 Hz), 4.081(1H, s), 3.809(3H, s), and 3.516(3H, s); $^{13}$C NMR(MeSO$_4^-$ salt, acetone, d$_b$) δ142.08(s), 138.97(s), 137.53(s), 136.21(d), 131.05(s), 127.95(d), 126.99(s), 126.09(s), 125.60(d), 123.39(d), 121.90(d), 121.38(d×2), 119.52(d), 117.11(s), 115.03(d), 113.37(d), 101.19(s), 96.07(s), 53.61(l), 36.39(q), 35.07(q), and 34.07(q).

Tetramethylnortopsentin B (MeSO$_4^-$ salt), colorless needles, recrystallized from chloroform/ethyl acetate in a freezer; MP 155°-165° C.; HREIMS m/z 418.0786 (calcd. for C$_{22}$H$_{19}$N$_4$Br=M$^+$+H—CH$_3$, Δ0.8 mmu); LREIMS m/z 420.0(100.0), 418.3(98.7), 405.0(13.9), 403.0(13.9), 340.0(12.0), 209.9(19.8), 208.9(21.1), 183.0(27.0), 169.0(24.4), 162.0(7.9), 156.0(10.1), 148.5(11.7), 142.0(19.0), 128.0(7.4), 115.1(14.2), 101.0(5.6), 82.0(14.1), 79.8(15.4), 52.0(22.9), and 49.8(68.5 rel. %); UV(Cl$^-$ salt, MeOH) λmax 199.0(ε37,100), 220.5(ε48,300), 268(sh), 286.5(ε20,300), 294.0(ε20,800), and 312(sh) nm; IR(Cl$^-$ salt, KBr), 1624, 1610(sh), 1578, 1560, 1527, 1500, 1464, 1450(sh), 1420, 1363, 1334, 1296, 1250, 1225, 1189, 1159, 1133, 1103(sh), 1094, 1051, 1013, 965, 935, 810, and 746 cm$^{-1}$; $^1$H NMR(MeSO$_4^-$ salt, chloroform-d) δ8.731(1H, s), 7.673(1H, s), 7.630(1H, d, J=1.7 Hz), 7.607(1H, brd, J=7.4 Hz), 7.374(1H, dd, J=8.5, 1.7 Hz), 7.299(1H, ddd, J=8.1, 7.0, 1.1 Hz), 7.270(1H, d, J=8.5 Hz), 7.215(1H, ddd, J=8.1, 6.9, 1.2 Hz), 3.954(3H, s), 3.861(3H, s), 3.836(3H, s), 3.717(3H, s), and 3.680(3H, s); $^{13}$C NMR(MeSO$_4^-$ salt, chloroform-d) δ141.49(s), 137.85(s), 136.86(s), 136.40(d), 131.14(d), 130.13(s), 126.57(s), 125.26(d), 124.66(s), 122.86(d), 121.09(d), 120.34(d), 119.73(d), 118.79(d), 116.86(s), 114.09(d), 110.12(d), 99.05(s), 94.47(s), 54.27(q), 36.25(q), 34.78(q), 33.80(q), and 33.22(q).

EXAMPLE 7—P388 IN VITRO ANTITUMOR SCREEN

Cell culture.

P388 murine leukemia cells, obtained from the National Cancer Institute, Bethesda, MD, were maintained at 37° C. in 5% CO$_2$ in humidified air. Growth medium was Roswell Park Memorial Institute medium 1640 supplemented with 10% heat-inactivated horse serum. Stock cultures of P388 cells were grown in antibiotic-free growth medium and were subcultured (10$^5$ cells/ml, 25 ml cultures in T-25 plastic tissue culture flasks) every 2-3 days. Every 3-4 months, stock cultures were re-initiated from frozen cells that were demonstrated to be free of mycoplasma contamination. To determine if organisms possess compounds having activity against P388 cells, extracts were diluted in methanol and added to cultures of P388 cells. An appropriate volume of the dilution was transferred to duplicate wells in a 96-well plate, evaporated to dryness, and 200 μl of growth medium-containing cells at a density of 1×10$^5$ cells/ml were added per well (final concentration of extract was 20 μg/ml). Each plate included six wells containing untreated cells for control growth (mean generation time was 15.2±0.7 hour, n=26 separate determinations) and replicate wells containing fluorouracil (0.2 μg/ml, ca. 95% inhibition of cell replication) as a positive control. For daily quality control, each technician determines the IC$_{50}$ of fluorouracil for inhibition of P388 cell proliferation. After 48-hour incubations, cell number was determined with the MTT assay (below), calculated as a percent of untreated cell growth, converted to percent inhibition, and reported to the chemist requesting the screen.

Determination of IC$_{50}$ values.

The initial determination of an IC$_{50}$ value for inhibition of P388 cell proliferation with a crude, semipure, or pure sample was made by diluting the sample in methanol to the appropriate concentration, and then serial 1:1 dilutions were made in duplicate in a 96-well plate, such that the final concentrations in the assay were 20, 10, 5, 1.25, and 0.625 μg/ml. After solvent was evaporated to dryness, cells were added to each well as described above. After 48-hour incubations, cell numbers were determined with the MTT assay, converted to percent control, and plotted versus the log of the sample concentration. Curves were fitted by least-squares linear regression of logit-transformed data and the concentration of sample that inhibited cell proliferation by 50% was reported to the chemist requesting the screen. If the $IC_{50}$ value was less than 0.625 μg/ml, additional serial dilutions were made and tested for activity.

MTT assay for cell number.

MTT or 3-(4,5-dimethylthiazol-2-yl)-2,5-diphenyltetrazolium bromide is used in an established method (J. Immunol. Methods [1983] 65:55-63) to enumerate cells rather than "Coulter counting." For screening purposes, the correlation between percent inhibition determined for actual crude extracts with the Coulter counter and MTT method was very good (r=0.953, n=102 separate determinations of activity at 20 μg/ml), and no extract that was positive as determined by actual cell counts was lost using the MTT assay. Additional results indicated that the MTT assay yielded very similar values for $IC_{50}$'s in parallel determination with Coulter counting. The results of the P388 assay are shown in Table 1.

TABLE 1

| Sample | Antitumor P388 $IC_{50}$, μg/ml |
|---|---|
| Nortopsentin A | 7.6 |
| Nortopsentin B | 7.8 |
| Nortopsentin C | 1.7 |
| Trimethylnortopsentin B (chloride salt) | 0.9 |
| Tetramethylnortopsentin B | 0.34 |

As can be seen from Table 1, each of the compounds tested showed antitumor activity.

ANTIMICROBIAL PROTOCOLS

Preparation of inocula.

Unless otherwise noted, all media were autoclaved at 121° C. for 15 minutes.

*Candida albicans*: C. albicans (ATCC strain 44506 was grown on Sabouraud dextrose agar to produce single colonies, one of which was used to inoculate Sabouraud dextrose broth. The broth was incubated at 37° C. with shaking at 200 rpm for 18 hours. The resultant culture was brought to 10% (v/v) glycerol, frozen at −80° C., and used as the inoculum for the anti-Candida assay.

Bacillus subtilis:

Standard spore stocks (ATCC strain 6633 were purchased from Difco (#0453-36-0).

Assay protocols.

1. Disc diffusion assay

*C. albicans* was inoculated into either melted Sabourand dextrose agar or RPMI-1640 in 2% agar at 45° C. to give a cell density of approximately 10,000 cells/mL. Plates were prepared with 10 mL of the seeded agar in a 10 cm×10 cm petri dish. These plates were stored at 4° C. until needed for the assay.

*B. subtilis* was inoculated into Penassay medium (1 mL of stock per 200 mL agar), melted, and cooled to 45° C. Plates were poured as described above.

Paper discs (6.35 mm) were impregnated with the test substance and allowed to dry. They were then placed onto the surface of a test plate prepared as detailed above. Plates were incubated overnight at 37° C., after which time the zones of growh inhibition could be read. These were expressed as the diameter of the zone in millimeters. Standard drugs were used in all cases.

2. MIC protocol

Two-fold dilutions of the test compound were prepared in 50 μL volumes of a suitable solvent using 96-well microtiter plates. In a separate 96-well plate, 35 μL volumes of either Sabouraud dextrose broth or RPMI-1640 were placed in each well. The test compound (5 μL) was then transferred to the broth. An inoculum of *C. albicans* in the appropriate medium was added to give a cell density of 1000 cells/mL and a total volume of 50 μL. Plates were incubated at 37° C. overnight. 10 μL of triphenyl tetrazolium chloride (1 w/v; filter sterilized) was then added to each well; a further 2-hour incubation resulted in a deep coloration of the microorganism. The MIC is the lowest concentration of the drug which completely inhibited growth.

TABLE 2

| | Antimicrobial | |
|---|---|---|
| | Bacillus subtilis zone (20 μg/disc) | Candida albicans MIC, μg/ml |
| Nortopsentin A | 8 | 3.1 |
| Nortopsentin B | 9 | 6.2 |
| Nortopsentin C | 9 | 12.5 |
| Trimethylnortopsentin B (chloride salt) | 11 | >50.0 |
| Tetramethlynortopsentin B | 12 | >50.0 |

As can be seen in Table 2, the novel compounds showed activity against microbes.

The compounds of the invention are useful for various non-therapeutic and therapeutic purposes. It is apparent from the testing the the compounds of the invention are effective for inhibiting microbial growth and for controlling microbial diseases. Also, because of the antimicrobial properties of the compounds, they are useful to swab laboratory benches and equipment in a microbiology laboratory to eliminate the presence of microbes, or they can be used as ultraviolet screeners in the plastics industry since they effectively absorb UV rays. As disclosed herein, they are also useful prophylactically and therapeutically for treating microbial infections in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, health, weight, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

We claim:

1. A compound having the following structure:

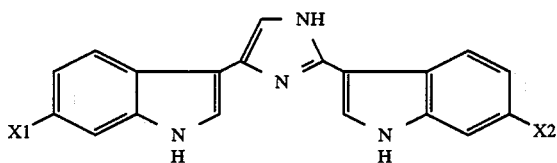

and selected from the group consisting of:

|  | X1 | X2 |
| --- | --- | --- |
| Nortopsentin A | Br | Br |
| Nortopsentin B | H | Br |
| Nortopsentin C | Br | H |
| Nortopsentin D | H | H, | or a salt of nortopentin A, B, C, or D.

2. The compound, according to claim 1, designated nortopsentin A, wherein X1 is Br and X2 is Br.

3. The compound, according to claim 1, designated nortopsentin B X1 is H and X2 is Br.

4. The compound, according to claim 1, designated nortopsentin C X1 is Br and X2 is H.

5. The compound, according to claim 1, designated nortopsentin D, wherein X1 is H and X2 is H.

6. Simple salts of the compounds of claim 1 wherein said salts are selected from the group consisting of $Cl^-$, $Br^-$, $I^-$, and $HSO_4^-$.

7. A compound selected from the group consisting of trimethylnortopsentin B and tetramethylnortopsentin B.

8. The compound, according to claim 7, wherein said compound is trimethylnortopsentin B.

9. The compound, according to claim 7, wherein said compound is tetramethylnortopsentin B.

10. A pharmaceutical composition for inhibiting tumor growth, said composition comprising a tumor-growth inhibiting amount of one or more compounds selected from the group consisting of nortopsentin A, nortopsentin B, nortopsentin C, nortopsentin D, trimethylnortopsentin B chloride salt, and tetramethylnortoposentin B, and a non-toxic pharmaceutically acceptable carrier or diluent.

11. A method for inhibiting microbial growth, said method comprising the application, to a person, animal, or surface hosting microbial growth, of a microbial growth inhibiting amount of a compound selected from the group consisting of nortopsentin A, nortopsentin B, nortopsentin C, nortopsentin D, trimethylnortopsentin B, and tetramethylnortopsentin B and a non-toxic pharmaceutically acceptable carrier or diluent.

12. The method, according to claim 11, wherein said compound is nortopsentin A.

13. The method, according to claim 11, wherein said compound is nortopsentin B.

14. The method, according to claim 11, wherein said compound is nortopsentin C.

15. The method, according to claim 11, wherein said compound is nortopsentin D.

16. The method, according to claim 11, wherein said compound is trimethylnortopsentin B.

17. The method, according to claim 11, wherein said compound is tetramethylnortopsentin B.

18. A method for inhibiting tumor growth, said method comprising the administration, to a person or animal in need of tumor growth inhibition, of a tumor-growth inhibiting amount of a compound selected from the group consisting of nortopsentin A, nortopsentin B, nortopsentin C, nortopsentin D, trimethylnortopsentin B, and tetramethylnortopsentin B, and a non-toxic pharmaceutically acceptable carrier or diluent.

19. The method, according to claim 18, wherein said compound is nortopsentin A.

20. The method, according to claim 18, wherein said compound is nortopsentin B.

21. The method, according to claim 18, wherein said compound is nortopsentin C.

22. The method, according to claim 18, wherein said compound is nortopsentin D.

23. The method, according to claim 18, wherein said compound is trimethylnortopsentin B.

24. The method, according to claim 18, wherein said compound is tetramethylnortopsentin B.

* * * * *

UNITED STATES PATENT AND TRADEMARK OFFICE
CERTIFICATE OF CORRECTION

PATENT NO. : 4,970,226

DATED : November 13, 1990

INVENTOR(S) : H. Howard Sun, Shinichi Sakemi, Sarath Gunasekera, Yoel Kashman, May Lui, Neal Burres, Peter McCarthy It is certified that error appears in the above-identified patent and that said Letters Patent is hereby corrected as shown below:

Column 5:   lines 56-57: "4.081(1H, s), 3.809(3H, s)," should read -- 4.081(1H, s), 3.971(3H, s), 3.809(3H, s),--.

Column 7:   lines 52-53: "Sabourand" should read --Sabouraud--.

Column 9:   line 19: "nortopentin" should read --nortopsentin--.

Signed and Sealed this

Seventeenth Day of March, 1992

Attest:

HARRY F. MANBECK, JR.

Attesting Officer

Commissioner of Patents and Trademarks